US006451733B1

United States Patent
Pidskalny et al.

(10) Patent No.: US 6,451,733 B1
(45) Date of Patent: Sep. 17, 2002

(54) SYNERGISTIC HERBICIDAL METHODS AND COMPOSITIONS

(75) Inventors: Ronald Steven Pidskalny; Roy Allan Killins, both of Alberta (CA)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/687,901

(22) Filed: Oct. 13, 2000

Related U.S. Application Data

(60) Provisional application No. 60/159,383, filed on Oct. 14, 1999.

(51) Int. Cl.[7] ............................................... A01N 43/40
(52) U.S. Cl. ....................................................... 504/130
(58) Field of Search ......................................... 504/130

(56) References Cited

U.S. PATENT DOCUMENTS

| | | | |
|---|---|---|---|
| 4,427,440 A | 1/1984 | von der Osten et al. | 71/94 |
| 5,294,597 A | 3/1994 | Foster et al. | 504/255 |
| 5,296,449 A | 3/1994 | Ryan et al. | 504/105 |
| 5,674,807 A | 10/1997 | Baltruschat | 504/130 |
| 6,030,924 A * | 2/2000 | Mayer et al. | 504/116 |

FOREIGN PATENT DOCUMENTS

| | | | |
|---|---|---|---|
| EP | 0188815 | 7/1986 | A01N/47/30 |
| EP | 0273668 | 7/1988 | A01N/43/40 |
| WO | 94/07368 | 4/1994 | A01N/43/40 |
| WO | 01/01777 A1 | 1/2001 | A01N/25/02 |

OTHER PUBLICATIONS

British Crop Protection Council: "The Pesticide Manual, Tenth Edition" Pesticide Manual, GB, Farnham, BCPC, vol. Ed. 10 pp. 1135–1341.
White,et al., AC 900001: A new herbicide for broadleaf weed control in cereals, Abstract No. XP–002161327.
Sandman, G. et al, "Phytoene Desaturase, the Essential Target for Bleaching Herbicides", Weed Science vol. 39, 1991, pp. 474–479.
J. F. Salembier, "Research on the Complementation of Isoproturon and Foliar Anti–Grass Herbicides", Database accession No. 1991–82508 XP002170514 Abstract.
R. White et al, "AC 900001:a new herbicide for broadleaf week control in cereals.", Proc. Br. Crop Prot. Conf. Weeds (1999) vol. 1, pp. 47–52.

\* cited by examiner

*Primary Examiner*—S. Mark Clardy
(74) *Attorney, Agent, or Firm*—Keil & Weinkauf

(57) ABSTRACT

The present invention provides a method for the synergistic control of undesirable plants such as Polygonum, Kochia, Galeopsis, Galium, Stelaria, Sinapis, and Avena which comprises applying to the plants or their locus a synergistically effective amount of an aryloxypicolinamide herbicide in combination with one or two selected additional herbicidal compounds. Further provided are synergistic herbicidal compositions comprising an aryloxypicolinamide herbicide and one or two selected additional herbicidal compounds.

20 Claims, No Drawings

SYNERGISTIC HERBICIDAL METHODS AND COMPOSITIONS

This application claims benefit of Provisional application Serial No. 60/159,383 filed Oct. 14, 1999.

BACKGROUND OF THE INVENTION

Aryloxypicolinamides such as those described in U.S. Pat. No. 5,294,597 demonstrate excellent herbicidal activity, in particular against broadleaf weeds in cereal crops. However, said aryloxypicolinamides, when used as the sole active ingredient, do not always achieve effective control of the full spectrum of weed species encountered in commercial agronomic practice at application rates required for acceptable crop safety. Such gaps in the spectrum of control can often be remedied by co-treatment with another herbicide known to be effective against the relevant weed species. It has been disclosed (U.S. Pat. No. 5,674,807) that selected combinations of aryloxypicolinamides produce not merely the expected additive effect, but may exhibit a significant synergistic effect (i.e., the combination shows a much higher level of activity than that which could be predicted from that of the individual components). This synergistic effect enables a greater margin of safety for the crop species. However, the disclosure is limited to two-way combinations of aryloxypicolinamides and members of selected known chemical classes which do not include herbicidal partners in the imidazolinone, cyclohexanedione, aryloxyphenoxypropionic acid, or pyridinecarboxylic acid classes. Moreover, although the phenoxyacetic acid chemical class is disclosed, 2,4-dichlorophenoxyacetic acid (2,4-D) is not specifically exemplified.

Therefore it is an object of this invention to provide synergistic, crop-selective herbicidal combinations with broad-spectrum weed control.

It is another object of this invention to provide herbicidal compositions useful for the synergistic control of a broad-spectrum of weeds in the presence of a crop.

SUMMARY OF THE INVENTION

Although aryloxypicolinamide compounds demonstrate excellent herbicidal activity, when applied alone they do not always achieve the desired spectrum of weed control at rates required for acceptable crop safety. Surprisingly, it has now been found that a two-way combination comprising an aryloxypicolinamide compound of formula I

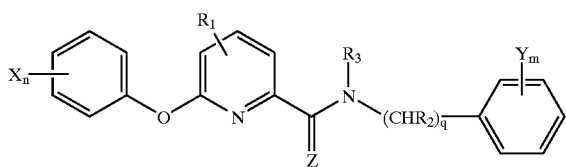

I wherein

Z represents an oxygen or sulfur atom;

$R_1$ represents a hydrogen or halogen atom or an alkyl or haloalkyl group;

$R_2$ represents a hydrogen or an alkyl group;

q is 0 or 1;

$R_3$ represents a hydrogen or an alkyl or alkenyl group;

the or each group X independently represents a halogen atom or an optionally substituted alkyl or alkoxy group, preferably a haloalkyl group, or an alkenyloxy, cyano, carboxy, alkoxycarbonyl, (alkylthio)carbonyl, alkylcarbonyl, amido, alkylamido, nitro, alkylthio, haloalkylthio, alkenylthio, alkynylthio, alkylsulphinyl, alkylsulphonyl, alkyloxyminoalkyl or alkenyloximinoalkyl group;

n is 0 or an integer from 1 to 5;

the or each group Y independently represents a halogen atom or an alkyl, nitro, cyano, haloalkyl, alkoxy or haloalkoxy group; and m is 0 or an integer from 1 to 5 plus a second herbicide selected from 2,4-dichlorophenoxyacetic acid (2,4-D), an imidazolinone, a cyclohexanedione, an aryloxyphenoxypropionic acid, or a pyridinecarboxylic acid herbicide demonstrates a synergistic herbicidal effect. Further, unexpectedly, a selected three-way combination comprising an aryloxypicolinamide compound of formula I and 2,4-D and a third herbicide selected from the group consisting of an imidazolinone, a cyclohexanedione, and an aryloxyphenoxypropionic acid herbicide produces a significant synergistic effect. Advantageously, the synergistic two-way and three-way combinations of the invention allow for lower application rates of said aryloxypicolinamide with concomitant increased spectrum of weed control. Moreover, the synergistic herbicidal methods and compositions of the invention allow for effective resistance management.

The present invention provides a method for the synergistic control of undesirable plants such as Polygonum, Kochia, Galeopsis, Galium, Stelaria, Sinapis, and Avena which comprises applying to the locus of said plants or to the foliage or stems of said plants a synergistically effective amount of a two-way combination comprising an aryloxypicolinamide compound of formula I plus a second herbicide selected from 2,4-D, an imidazolinone, a cyclohexanedione, an aryloxyphenoxypropionic acid, or a pyridinecarboxylic acid herbicide. The present invention also provides a method for the synergistic control of undesirable plants which comprises applying to the locus of said plants a synergistically effective amount of a three-way combination comprising an aryloxypicolinamide compound of formula I, 2,4-D, and a third herbicide selected from the group consisting of an imidazolinone, a cyclohexanedione, or an aryloxyphenoxypropionate herbicide.

The present invention also provides a synergistic herbicidal composition which comprises an agriculturally acceptable carrier and a synergistically effective amount of a two-way combination of an aryloxypicolinamide compound of formula I plus a second herbicide selected from 2,4-D, an imidazolinone, a cyclohexanedione, an aryloxyphenoxypropionic acid, or a pyridinecarboxylic acid herbicide; or a three-way combination of an aryloxypicolinamide compound of formula I, 2,4-D, and a third herbicide selected from the group consisting of an imidazolinone, a cyclohexanedione, and an aryloxyphenoxypropionate herbicide.

DETAILED DESCRIPTION OF THE INVENTION

Aryloxypicolinamides of formula I

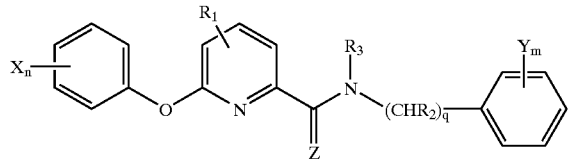

wherein Z, $R_1$, $R_2$, $R_3$, X, n, Y and m are defined herein above and methods for their preparation are described in U.S. Pat. No. 5,294,597. Said aryloxypicolinamides demonstrate excellent herbicidal activity, in particular against broadleaf weeds in cereal crops. However, said aryloxypicolinamides when used as the sole active ingredient do not always achieve effective control of the full spectrum of weed species encountered in commercial agronomic practice, in conjunction with reliable selectivity for the crop species.

Surprisingly, it has now been found that a two-way combination of an aryloxypicolinamide of formula I and a second herbicide selected from 2,4-D, an imidazolinone, a cyclohexanedione, an aryloxyphenoxypropionic acid, or a pyridinecarboxylic acid herbicide provides synergistic control of troublesome weeds such as Polygonum, Kochia, Galeopsis, Galium, Stelaria, Sinapis, and Avena. Also, surprisingly, a three-way combination of an aryloxypicolinamide of formula I and 2,4-D plus a third herbicidal compound selected from the group consisting of an imidazolinone, a cyclohexanedione, and an aryloxyphenoxypropionic acid herbicide provides synergistic weed control. That is, the application of the two-way or three-way combinations of the invention gives a mutual reinforcing action such that the application rates of the individual herbicidal components can be reduced and still the same herbicidal effect is achieved or, alternatively, the application of the combination of herbicidal components demonstrates a greater herbicidal effect than expected from the effect of the application of the individual herbicidal components when applied singly at the rate at which they are present in the combination (synergistic effect).

In the specification and claims, the term 2,4-D designates 2,4-dichlorophoxyacetic acid. Examples of an imidazolinone herbicide suitable for use in the methods and compositions of the invention include imazapyr, imazethapyr, imazapic, imazaquin, imazamox, imazamethabenz methyl, or the like, preferably imazamethabenz methyl.

A cyclohexanedione herbicide suitable for use in the methods and compositions of the invention include sethoxydim, clethodim, alloxydim, tralkoxydim, cycloxydim, or the like, preferably tralkoxydim.

Exemplary of aryloxyphenoxypropionate herbicides suitable for use in the inventive methods and compositions are diclofop methyl, fluazifop-p-butyl, fenoxaprop-ethyl, fenoxaprop-p-ethyl, quizalofop-p-terfuryl, quizalofop-p, haloxyfop-methyl, clodinafop-propargyl, isoxapurifop, cyhalofop butyl, fenthioprop, propaquizafop, or the like, preferably fenoxaprop-p-ethyl.

A pyridinecarboxylic acid herbicide such as picloran, clopyralid, or the like, preferably clopyralid, is suitable for use in the two-way combination of the invention.

Preferred synergistic combinations of the invention are those two-way or three-way combinations containing a formula I aryloxypicolinamide wherein Z is oxygen;
$R_1$ is hydrogen;
q is 0;
$R_3$ is hydrogen;
X is haloalkyl; and
Y is hydrogen or fluorine.

More preferred synergistic two-way and three-way combinations are those wherein the formula I compound is N-(4-fluorophenyl)-6-[3-trifluoromethyl)phenoxy]-2-pyridine carboxamide ilustrated below, and hereinafter designated, picolinafen.

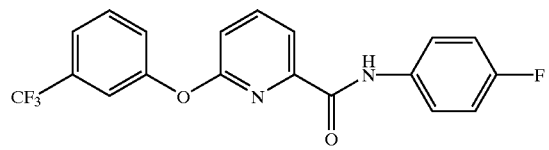

picolinafen

Preferred second herbicides for the two-way combinations of the invention are 2,4-D, imazamethabenz methyl, tralkoxydim, fenoxaprop-p-ethyl, and clopyralid.

Preferred third herbicides for the three-way combination of the invention are imazamethabenz methyl, tralkoxydim or fenoxaprop-p-ethyl.

In actual practice, the combination of the invention may be applied simultaneously (as a tank mix or a premix), separately or sequentially.

Thus, in accordance with the method of invention a synergistically effective amount of a two-way combination of aryloxypicolinamide and a second herbicide selected from 2,4-D, an imidazolinone, a cyclohexanedione, an aryloxyphenoxypropionic acid, or a pyridinecarboxylic acid herbicide; or a synergistically effective amount of a three-way combination of an aryloxypicolinamide, 2,4-D, and a third herbicide selected from an imidazolinone, a cyclohexanedione, or an aryloxyphenoxypropionate is applied to the locus, foliage or stems of undesirable plants, particularly plants selected from the genera Polygonum, Kochia, Galeopsis, Galium, Stelaria, Sinapis, and Avena, optionally in the presence of a crop, preferably a cereal crop such as wheat, barley, rice, corn, rye or the like.

The synergistically effective amount of the two- and three-way combinations described above may vary according to prevailing conditions such as the particular second and third component present, weed pressure, application timing, weather conditions, soil conditions, mode of application, topographical character, target crop species and the like.

More preferred two-way combinations of the invention are those wherein the weight/weight ratio of picolinafen to the second component is about:

picolinafen:2,4-D, 1:1 to 1:25;
picolinafen:imazethabenz methyl, 1:1 to 1:35;
picolinafen:tralkoxydim, 1:1 to 1:20;
picolinafen:fenoxaprop-p-ethyl, 1:1 to 1:10; or
picolinafen:clopyralid, 1:1 to 1:15.

More preferred three-way combinations of the invention are those wherein the weight/weight/weight ratio of picolinafen to 2,4-D to third component is about:

picolinafen:2,4-D:imazamethabenz methyl, 1:1:1 to 1:35:25 picolinafen:2,4-D:tralkoxydim, 1:1:1 to 1:20:25; or picolinafen:2,4-D:fenoxaprop-p-ethyl, 1:1:1 to 1:10:25.

The present invention also provides a synergistic herbicidal composition comprising an agriculturally acceptable carrier and a synergistically effective amount of a two-way combination of an aryloxypicolinamide of formula I and a second herbicidal compound selected from the group consisting of 2,4-D, an imidazolinone herbicide, a cyclohexanedione herbicide, an aryloxyphenoxypropionic acid herbicide and a pyridinecarboxylic acid herbicide. The present invention further provides a synergistic herbicidal composition which comprises an agriculturally acceptable carrier and a synergistically effective amount of a three-way combination of an aryloxypicolinamide compound of formula I, 2,4-D, and a third herbicidal compound selected from the group consisting of an imidazolinone herbicide, a cyclohexanedione herbicide, and an aryloxyphenoxypropionate herbicide.

The agriculturally acceptable carrier may be a solid or a liquid, preferably a liquid, more preferably water. While not required, the combination compositions of the invention may also contain other additives such as fertilizers, inert formulation aids, i.e. surfactants, emulsifiers, defoamers, dyes, extenders or any of the conventional inert ingredients typically employed in herbicidal formulated products.

Compositions according to the invention may be formulated in any conventional form, for example in the form of a twin pack, or as an aqueous concentrate, soluble granular, dispersible granular or the like.

Preferred two-way combination compositions of the invention are those compositions wherein the aryloxypicolinamide compound is picolinafen. Also preferred are those synergistic two-way combination compositions having a second herbicide selected from the group consisting of 2,4-D, imazamethabenz methyl, tralkoxydim, fenoxaprop-p-ethyl and clopyralid. More preferred two-way combination compositions of the invention are those compositions of the invention wherein the weight/weight ratio of picolinafen to second component is about:

picolinafen:2,4-D, 1:1 to 1:25;

picolinafen:imazethabenz methyl, 1:1 to 1:35;

picolinafen:tralkoxydim, 1:1 to 1:20;

picolinafen:fenoxaprop-p-ethyl, 1:1 to 1:10; or picolinafen:clopyralid, 1:1 to 1:15.

Preferred three-way combination compositions of the invention are those compositions wherein the picolinamide compound is picolinafen. Also preferred are those synergistic three-way combination compositions having a third herbicide selected from the group consisting of imazamethabenz methyl, tralkoxydim and fenoxaprop-p-ethyl. More preferred three-way combination compositions of the invention are those compositions wherein the weight/weight/weight ratio of picolinafen to 2,4-D to third component is about:

picolinafen:2,4-D:imazamethabenz methyl, 1:1:1 to 1:35:25 picolinafen:2,4-D:tralkoxydim, 1:1:1 to 1:20:25; or picolinafen:2,4-D:fenoxaprop-p-ethyl, 1:1:1 to 1:10:25.

For a more clear understanding of the invention, specific examples thereof are set forth below. These examples are merely illustrative, and are not to be understood as limiting the scope and underlying principles of the invention in any way.

In the following examples, synergism for two-way combinations is determined by the Colby[1] method, i.e. the expected (or predicted) response of the combination is calculated by taking the product of the observed response for each individual component of the combination when applied alone divided by 100 and subtracting this value from the sum of the observed response for each component when applied alone. Synergism of the combination is then determined by comparing the observed response of the combination to the expected (or predicted) response as calculated from the observed responses of each individual component alone. If the observed response of the combination is greater than the expected (or predicted) response then the combination is said to be synergistic and falls within the definition of synergistic effect as previously defined.

[1] Colby, S. R., Weeds, 1967(15), p. 20–22

The foregoing is illustrated mathematically below, wherein a two-way combination, $C_2$, is composed of component X plus component Y and Obs. designates the observed response of the combination $C_2$.

$$(X + Y) - \frac{XY}{100} = \text{Expected response (Exp.)}$$

Synergism≡Obs.>Exp.

In similar manner for the case of three-way combination, $C_3$; is composed of component X plus component Y plus component X and Obs. designates the observed response of the combination $C_3$.

$$(X + Y + Z) - \frac{(XY + XZ + YZ)}{100} + \frac{ABD}{10000} = \text{Exp.}$$

Synergism≡Obs.>Exp.

In the following examples, crop tolerance ratings are taken periodically throughout the growing season. The first rating is taken one to two weeks after treatment and the final rating is taken just prior to harvest. For all treatments described in the following examples crop tolerance was commercially acceptable, i.e. ≦20% injury, on each of the three crops tested. None of the treatments demonstrated commercially unacceptable injury to barley, durum wheat or hard red spring wheat.

EXAMPLE 1

Evaluation of the Herbicidal Activity of a Combination of Picolinafen and 2,4-Dichlorophenoxyacetic Acid Grassy and broadleaved weeds are either seeded perpendicular to the direction of the crop or broadcast in early to mid-May. The crop is seeded after the weed seed. Row width is 18 cm. The seed is drilled in with a Roger's 1.8 m width drill to a depth of 5 cm.

All trials employ standard accepted weed science procedures. Applications are made with a Roger's $CO_2$-powered shrouded sprayer. Test design is a modified randomized complete block design with four replications. All applications are made post-emergence to the weeds and crop.

The test solutions are prepared by tank-mixing sufficient quantities of aqueous solutions and/or dispersions of the test compounds.

The treated plots are examined at intervals during the growing season and rated for percent control of weeds and crop injury. The data listed is an average of the replicates for that treatment. The Colby method of analysis is used to determine the resultant biological effect of the combination treatment as compared to the biological effect of each component when applied alone. The data are reported in Table I.

As can be seen from the data shown in Table I, application of a combination of picolinafen plus 2,4-D gave significantly greater weed control than that which could be predicted from the weed control resulting from the application of either picolinafen alone or 2,4-D alone.

TABLE I

Evaluation of the Herbicidal Activity of
a Combination of Picolinafen plus 2,4-D

| | Percent Control | | picolinafen + 2,4-D | |
|---|---|---|---|---|
| | picolinafen | 2,4-D | 50 g/ha + 280 g/ha | |
| Weed Species | 50 g/ha | 280 g/ha | Observed | Expected |
| Avena fatua | 5 | 2 | 15 | 7 |
| Chenopodium album | 57 | 91 | 97 | 96 |
| Polygonum convolvulus | 54 | 48 | 80 | 76 |
| Galeopsis tetrahit | 59 | 2 | 70 | 60 |
| Polygonum (smartweed) spp. | 26 | 53 | 85 | 65 |
| Vaccaria pyramaidata | 63 | 51 | 97 | 82 |

EXAMPLE 2

Evaluation of the Herbicidal Activity of a
Combination of Picolinafen and Imazamethabenz
Methyl Following essentially the same procedure described in Example 1 and employing picolinafen and imazamethabenz methyl, the data shown in Table II are obtained.

As can be seen from the data in Table II, the application of a combination of picolinafen plus imazamethabenz methyl gives significantly greater weed control than that which could be predicted from the weed control resulting from the application of either picolinafen alone or imazamethabenz methyl alone.

TABLE II

Evaluation of the Herbicidal Activity of a
Combination of Picolinafen plus Imazamethabenz Methyl

| | Percent Control | | picolinafen + imazamethabenz methyl | |
|---|---|---|---|---|
| | picolinafen | imazamethabenz methyl | 50 g/ha + 400 g/ha | |
| Weed Species | 50 g/ha | 400 g/ha | Observed | Expected |
| Avena fatua | 5 | 88 | 91 | 89 |
| Setaria viridis | 14 | 10 | 42 | 23 |
| Brassica napus (Imidazolinone tolerant) | 65 | 0 | 86 | 65 |
| Chenopodium album | 57 | 18 | 86 | 65 |
| Galeopsis tetrahit | 59 | 4 | 76 | 61 |
| Galium aparine | 28 | 48 | 90 | 63 |
| Polygonum spp. | 26 | 76 | 84 | 82 |
| Kochia scoparia | 59 | 31 | 85 | 72 |
| Salsola kali | 56 | 9 | 79 | 60 |
| Vaccaria pyramaidata | 63 | 20 | 77 | 70 |

EXAMPLE 3

Evaluation of the Herbicidal Activity of a
Combination of Picolinafen and Tralkoxydim Following essentially the same procedure as described in Example 1 and employing picolinafen and tralkoxydim, the data shown in Table III are obtained As can be seen from the data shown on Table III, the application of a combination of picolinafen plus tralkoxydim gives significantly greater weed control than that which could be predicted from the weed control resulting from the application of either picolinafen alone or tralkoxydim alone.

TABLE III

Evaluation of the Herbicidal Activity of a
Combination of Picolinafen plus Tralkoxydim

| | Percent Control | | picolinafen + tralkoxydim | |
|---|---|---|---|---|
| | picolinafen | tralkoxydim | 50 g/ha + 200 g/ha | |
| Weed Species | 50 g/ha | 200 g/ha | Observed | Expected |
| Avena fatua | 5 | 97 | 98 | 97 |
| Sinapis arvensis | 78 | 0 | 94 | 78 |
| Brassica napus | 70 | 0 | 95 | 70 |
| Brassica napus (imidazolinone tolerant) | 65 | 0 | 92 | 65 |
| Amaranthus retroflexus | 90 | 1 | 98 | 90 |
| Chenopodium album | 57 | 0 | 93 | 57 |

TABLE III-continued

Evaluation of the Herbicidal Activity of a
Combination of Picolinafen plus Tralkoxydim

| | Percent Control | | picolinafen + tralkoxydim | |
|---|---|---|---|---|
| | picolinafen | tralkoxydim | 50 g/ha + 200 g/ha | |
| Weed Species | 50 g/ha | 200 g/ha | Observed | Expected |
| Polygonum convolvulus | 54 | 0 | 87 | 54 |
| Vaccaria pyramaidata | 63 | 0 | 86 | 63 |

EXAMPLE 4

Evaluation of the Herbicidal Activity of a Combination of Picolinafen and Fenoxaprop-p-ethyl Following essentially the same procedure as described in Example 1 and employing picolinafen and fenoxaprop-p-ethyl, the data shown in Table IV are obtained.

As can be seen from the data shown on Table IV, the application of a combination of picolinafen plus fenoxaprop-p-ethyl gives significantly greater weed control than that which could be predicted from the weed control resulting from the application of either picolinafen alone or fenoxaprop-p-ethyl alone.

TABLE IV

Evaluation of the Herbicidal Activity of a
Combination of Picolinafen plus Fenoxaprop-p-ethyl

| | Percent Control | | picolinafen + fenoxaprop-p-ethyl | |
|---|---|---|---|---|
| | picolinafen | fenoxaprop-p-ethyl | 50 g/ha + 72 g/ha | |
| Weed Species | 50 g/ha | 72 g/ha | Observed | Expected |
| Sinapis arvensis | 78 | 0 | 96 | 78 |
| Setaria viridis | 14 | 98 | 99 | 98 |
| Brassica napus | 70 | 0 | 97 | 70 |
| Brassica napus (imidazolinone tolerant) | 65 | 0 | 97 | 65 |
| Amaranthus retroflexus | 90 | 9 | 94 | 91 |
| Chenopodium album | 57 | 0 | 95 | 57 |
| Polygonum convolvulus | 54 | 0 | 74 | 54 |
| Vaccaria pyramaidata | 63 | 0 | 71 | 63 |

EXAMPLE 5

Evaluation of the Herbicidal Activity of a Combination of Picolinafen and Clopyralid Following essentially the same procedure as in Example 1 and employing picolinafen and clopyralid, the data shown in Table V are obtained.

As can be seen from the data shown on Table IV the application of a combination of picolinafen plus clopyralid gives significantly greater weed control than that which could be predicted from the weed control resulting from the application of either picolinafen alone or clopyralid alone.

TABLE V

Evaluation of the Herbicidal Activity of a
Combination of Picolinafen plus Clopyralid

| | Percent Control | | picolinafen + clopyralid | |
|---|---|---|---|---|
| | picolinafen | clopyralid | 50 g/ha + 150 g/ha | |
| Weed Species | 50 g/ha | 150 g/ha | Observed | Expected |
| Sinapis arvensis | 78 | 16 | 87 | 82 |
| Brassica napus | 70 | 12 | 78 | 74 |
| Brassica napus (imidazolinone tolerant) | 65 | 8 | 85 | 68 |
| Chenopodium album | 57 | 51 | 83 | 79 |
| Stellaria media | 64 | 10 | 70 | 68 |
| Galium aparine | 28 | 0 | 30 | 28 |

EXAMPLE 6

Evaluation of the Herbicidal Activity of a Combination of Picolinafen, Imazamethabenz Methyl and 2,4-D Following essentially the same procedure as described in Example 1 and employing picolinafen, 2,4-D and imazamethabenz methyl, the data shown in Table VI are obtained.

As can be seen from the data on Table VI, the application of a combination of picolinafen, 2,4-D and imazamethabenz methyl gives significantly greater weed control than that which could be predicted from the weed control resulting from the application of picolinafen alone, 2,4-D alone or imazamethabenz methyl alone.

TABLE VI

Evaluation of the Herbicidal Activity of a
Combination of Picolinafen, 2,4-D and Imazamethabenz Methyl

| | Percent Control | | | picolinafen + 2,4-D + imazamethabenz methyl 50 g/ha + 280 g/ha + 400 g/ha | |
|---|---|---|---|---|---|
| Weed Species | picolinafen | imazamethabenz methyl | 2,4-D | | |
| | 50 g/ha | 400 g/ha | 280 g/ha | Observed | Expected |
| Avena fatua | 5 | 88 | 2 | 91 | 89 |
| Setaria viridis | 14 | 10 | 0 | 49 | 23 |
| Stellaria media | 64 | 8 | 10 | 86 | 70 |
| Galeopsis tetrahit | 59 | 4 | 2 | 82 | 61 |
| Galium aparine | 28 | 48 | 43 | 94 | 79 |
| Polygonum spp. | 26 | 76 | 53 | 99 | 92 |
| Kochia scoparia | 59 | 31 | 52 | 93 | 86 |
| Salsola kali | 56 | 9 | 35 | 97 | |
| Vaccaria pyramaidata | 63 | 20 | 51 | 93 | 74 |

EXAMPLE 7

Evaluation of the Herbicidal Activity of a Combination of Picolinafen, Tralkoxydim and 2,4-D Following essentially the same procedure as described in Example 1 and employing picolinafen, 2,4-D, and tralkoxydim, the data shown in Table VII are obtained.

As can be seen from the data on Table VII, the application of a combination of picolinafen, 2,4-D and tralkoxydim gives significantly greater weed control than that which could be predicted from the weed control resulting from the application of picolinafen alone, 2,4-D alone or tralkoxydim alone.

TABLE VII

Evaluation of the Herbicidal Activity of a Combination of Picolinafen plus 2,4-D and Tralkoxydim

| Weed Species | picolinafen 50 g/ha | tralkoxydim 200 g/ha | 2,4-D 280 g/ha | picolinafen + 2,4-D + tralkoxydim 50 g/ha + 200 g/ha + 280 g/ha | |
|---|---|---|---|---|---|
| | Percent Control | | | Observed | Expected |
| *Avena fatua* | 5 | 97 | 2 | 98 | 97 |
| *Sinapis arvensis* | 78 | 0 | 92 | 99 | 98 |
| *Brassica napus* | 70 | 0 | 93 | 100 | 98 |
| *Brassica napus* (imidazolinone tolerant) | 65 | 0 | 94 | 100 | 98 |
| *Chenopodium album* | 57 | 0 | 91 | 98 | 96 |
| *Polygonum convolvulus* | 54 | 0 | 48 | 90 | 76 |
| *Vaccaria pyramaidata* | 63 | 0 | 51 | 90 | 82 |

EXAMPLE 8

Evaluation of the Herbicidal Activity of a Combination of Picolinafen, 2,4-D and Fenoxaprop-p-ethyl Following essentially the same procedure as described in Example 1 and employing picolinafen, 2,4-D and fenoxaprop-p-ethyl, the data shown in Table VIII are obtained.

As can be seen from the data shown in Table VIII, the application of a combination of picolinafen, 2,4-D and fenoxaprop-p-ethyl gives significantly greater weed control than that which could be predicted from the weed control resulting from the application of picolinafen alone, or 2,4-D alone or fenoxaprop-p-ethyl alone.

TABLE VIII

Evaluation of the Herbicidal Activity of a Combination of Picolinafen, plus 2,4-D and Fenoxaprop-p-ethyl

| Weed Species | picolinafen 50 g/ha | fenoxaprop-p-ethyl 72 g/ha | 2,4-D 280 g/ha | picolinafen + 2,4-D + fenoxaprop p-ethyl 50 g/ha + 280 g/ha + 72 g/ha | |
|---|---|---|---|---|---|
| | Percent Control | | | Observed | Expected |
| *Brassica napus* | 70 | 0 | 93 | 100 | 98 |
| *Brassica napus* (imidazolinone tolerant) | 65 | 0 | 94 | 100 | 98 |
| *Chenopodium album* | 57 | 0 | 91 | 97 | 96 |
| *Polygonum convolvulus* | 54 | 0 | 48 | 93 | 76 |
| *Vaccaria pyramaidata* | 63 | 0 | 51 | 96 | 82 |

What is claimed is:

1. A method for the synergistic control of undesirable plants which comprises applying to the locus of said plants or to the foliage or stems of said plants a synergistically effective amount of a two-way combination of an aryloxypicolinamide of formula I

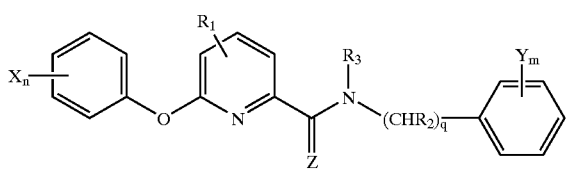

wherein
- Z represents an oxygen or sulfur atom;
- $R_1$ represents a hydrogen or halogen atom or an alkyl or haloalkyl group;
- $R_2$ represents a hydrogen or an alkyl group;
- q is 0 or 1;
- $R_3$ represents a hydrogen or an alkyl or alkenyl group;
- the or each group X independently represents a halogen atom or an optionally substituted alkyl or alkoxy group, preferably a haloalkyl group, or an alkenyloxy, cyano, carboxy, alkoxycarbonyl, (alkylthio) carbonyl, alkylcarbonyl, amido, alkylamido, nitro, alkylthio, haloalkylthio, alkenylthio, alkynylthio, alkylsulphinyl, alkylsulphonyl, alkyloxyiminoalkyl or alkenyloximinoalkyl group;
- n is 0 or an integer from 1 to 5;
- the or each group Y independently represents a halogen atom or an alkyl, nitro, cyano, haloalkyl, alkoxy or haloalkoxy group; and
- m is 0 or an integer from 1 to 5, and
- a second herbicide selected from the group consisting of an imidazolinone herbicide and a cyclohexanedione herbicide.

2. The method according to claim 1 having a aryloxypicolinamide of formula I wherein
- Z is oxygen;
- $R_1$ is hydrogen;
- q is 0;
- $R_3$ is hydrogen;
- X is haloalkyl; and
- Y is hydrogen or fluorine.

3. The method according to claim 2 wherein the formula I aryloxypicolinamide is picolinofen.

4. A method for the synergistic control of undesirable plants which comprises applying to the locus of said plaints, or to the foliage or stems of said plants a synergistically effective amount of a two-way combination of picolinafen and a second herbicide of 2,4-D or an aryloxyphenoxypropionate herbicide selected from the group consisting of fluazifop-p-butyl, fenoxaprop-ethyl, fenoxaprop-p-ethyl, quizalofop-p-terfuryl, quizalofop-p, haloxyfop-methyl, clodinaflop-propargyl, isoxapurifop, cyhalofop butyl, fenthioprop and propaquizaflop.

5. A method for the synergistic control of undesirable plants which comprises applying to the locus of said plaints, or to the foliage or stems of said plants a synergistically effective amount of a two-way combination of picolinafen and a second herbicide selected from the group consisting of picloran and clopyralid.

6. A method for the synergistic control of undesirable plants which comprises applying to the locus of said plants, or to the foliage or stems of said plants a synergistically effective amount of a two-way combination of picolinafen and a second herbicide of 2,4-D.

7. A method for the synergistic control of undesirable plants which comprises applying to the locus of said plants, or to the foliage or stems of said plants a synergistically effective amount of a two-way combination of picolinafen and a second herbicide selected from the group consisting of imazamethabenx methyl, tralkoxydim, fenoxaprop-p-ethyl or clopyralid.

8. A method for the synergistic control of undesirable plants which comprises applying to the locus of said plants or to the foliage or stems of said plants a synergistically effective amount of a three-way combination of an aryloxypicolinamide of formula I

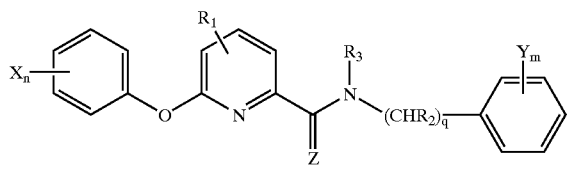

wherein
- Z represents an oxygen or sulfur atom;
- $R_1$ represents a hydrogen or halogen atom or an alkyl or haloalkyl group;
- $R_2$ represents a hydrogen or an alkyl group;
- q is 0 or 1;
- $R_3$ represents a hydrogen or an alkyl or alkenyl group;
- the or each group X independently represents a halogen atom or an optionally substituted alkyl or alkoxy group, preferably a haloalkyl group, or an alkenyloxy, cyano, carboxy, alkoxycarbonyl, (alkylthio) carbonyl, alkylcarbonyl, amido, alkylamido, nitro, alkylthio, haloalkylthio, alkenylthio, alkynylthio, alkylsulphinyl, alkylsulphonyl, alkyloxyiminoalkyl or alkenyloximinoalkyl group;
- n is 0 or an integer from 1 to 5;
- the or each group Y independently represents a halogen atom or an alkyl, nitro, cyano, haloalkyl, alkoxy or haloalkoxy group; and
- m is 0 or an integer from 1 to 5, and
- 2,4-D plus a third herbicide selected from the group consisting of an imidazolinone herbicide and a cyclohexanedione herbicide.

9. The method according to claim 8 having a formula I aryloxypicolinamide wherein
- Z is oxygen;
- $R_1$ is hydrogen;
- q is 0;
- $R_3$ is hydrogen
- X is haloalkyl; and
- Y is hydrogen or fluorine.

10. The method according to claim 9 wherein said formula I aryloxypicolinamide is picolinafen.

11. A method for the synergistic control of undesirable-plants which comprises applying to the locus of said plants or to the foliage or stems of said plants a synergistically effective amount of a three-way combination of picolinafen and 2,4-D plus a third herbicide selected from the group consisting of imazamethabenz methyl, tralkoxydim or fenoxaprop-p-ethyl.

12. A synergistic herbicidal composition which comprises an agriculturally acceptable carrier and a synergistically effective amount of a two-way combination of an aryloxypicolinamide of formula I

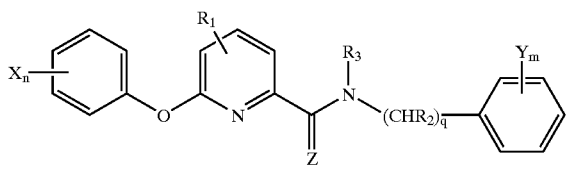

wherein X, Y, Z, $R_1$, $R_2$, $R_3$, m, n and q are as defined in claim 1 and a second herbicide selected from the group consisting of an imidazolinone herbicide and a cyclohexanedione herbicide.

13. The composition according to claim 12 having a formula I aryloxypicolinamide wherein Z is oxygen;
$R_1$ is hydrogen;
q is 0;
$R_3$ is hydrogen;
X is haloalkyl; and
Y is hydrogen or fluorine.

14. The composition according to claim 13 wherein said formula I aryloxypicolinamide is picolinafen.

15. A synergistic herbicidal composition which comprises an agriculturally acceptable carrier and a synergistically effective amount of a two-way combination of picolinafen and a second herbicide of 2,4-D or an aryloxyphenoxypropionate herbicide selected from the group consisting of fluazifop-p-butyl, fenoxaprop-ethyl, fenoxaprop-p-ethyl, quizalofop-p-terfurly, quizalofop-p, haloxyfop-methyl, clodinaflop-propargyl, isoxapurifop, cyhalofop butyl, fenthioprop and propaquizaflop.

16. A synergistic herbicidal composition which comprises an agriculturally acceptable carrier and a synergistically effective amount of a two-way combination of picolinafen and a second herbicide selected from the group consisting of picloran and clopyralid.

17. A synergistic herbicidal composition which comprises an agriculturally acceptable carrier and a synergistically effective amount of a three-way combination consisting essentially of: an aryloxypicolinamide of formula I

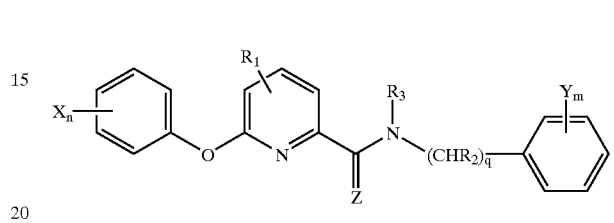

wherein X, Y, Z, $R_1$, $R_2$, $R_3$, m, n and q are as defined in claims 8; 2,4-D; and a third herbicide selected from an imidazolinone herbicide and a cyclohexanedione herbicide.

18. The composition according to claim 17 having a formula I aryloxypicolinamide wherein Z is oxygen;
$R_1$ is hydrogen;
q is 0;
$R_3$ is hydrogen;
X is haloalkyl; and
Y is hydrogen or fluorine.

19. The composition according to claim 18 wherein said formula I aryloxypicolinamide is picolinafen.

20. A synergistically herbicidal composition which comprises an agriculturally acceptable carrier and a synergistically effective amount of a three-way combination consisting essentially of picolinafen; 2,4-D; and a third herbicide selected from imazamethabenz methyl, tralkoxydim or fenoxaprop-p-ethyl.

* * * * *

UNITED STATES PATENT AND TRADEMARK OFFICE
CERTIFICATE OF CORRECTION

PATENT NO.   : 6,451,733 B1
DATED        : September 17, 2002
INVENTOR(S)  : Pidskalny et al.

It is certified that error appears in the above-identified patent and that said Letters Patent is hereby corrected as shown below:

Column 13,
Line 55, "plaints" should be -- plants --.
Line 66, "plaints" should be -- plants --.

Signed and Sealed this

Eleventh Day of February, 2003

JAMES E. ROGAN
*Director of the United States Patent and Trademark Office*